United States Patent [19]

Carpenter

[11] Patent Number: 5,139,654
[45] Date of Patent: Aug. 18, 1992

[54] LIQUID COLLECTOR PRESSURIZING AND FILTERING MEANS

[75] Inventor: Robert E. Carpenter, Nutley, N.J.

[73] Assignee: Norton Company, Worcester, Mass.

[21] Appl. No.: 601,531

[22] Filed: Oct. 22, 1990

[51] Int. Cl.$^5$ .............................................. G01N 1/00
[52] U.S. Cl. ................................. 210/136; 210/258;
210/416.1; 210/418; 210/419; 210/423;
210/435; 210/445; 210/446; 210/447; 73/863;
73/864.35; 73/864.62; 73/864.63; 73/864.74;
73/864.83; 73/864.91
[58] Field of Search ...................... 210/258, 416.1, 418,
210/419, 423, 435, 445, 446, 447, 136;
73/864.64, 864.67, 864.34, 864.51, 864.62,
864.63, 864.35, 864.81, 864.85, 864.86, 864.87,
864.91, 863.83, 863.84

[56] References Cited

U.S. PATENT DOCUMENTS

| | | | |
|---|---|---|---|
| 4,430,213 | 2/1984 | Isikawa | 210/136 |
| 4,590,810 | 5/1986 | Hunkin et al. | 73/864.63 |
| 4,807,707 | 2/1989 | Handley et al. | 73/864.74 |
| 4,928,541 | 5/1990 | Toon et al. | 73/864.63 |
| 4,949,582 | 8/1990 | Vollweiler | 73/864.63 |

Primary Examiner—Robert A. Dawson
Assistant Examiner—David Reifsnyder
Attorney, Agent, or Firm—Arthur A. Loiselle, Jr.

[57] ABSTRACT

Apparatus for quickly taking and filtering liquid taken from a body of liquid comprises a bailer for taking and containing a sample of the liquid therein. The bailer has an upper end portion adapted for quickly disconnecting and connecting a liquid pressurizing device including a hand operated fluid pump or regulated tank of compressed gas. A lower end portion of the bailer is provided with a ball or poppet check valve controlling the flow of liquid to and from the bailer by way of an internal opening adapted for quickly connecting and disconnecting a filtering unit to and from the bailer. The filtering unit has a disposable filter element inside of a housing attached to an upper adapter with a liquid passage therein quickly inserted into sealing engagement with the internal opening of the bailer and which opens the ball check valve. A lower end of the filter housing is connected by another adapter into which a flow control valve is quickly connected to and disconnectable from. A tubular needle or tube extends from the lower end of the flow control valve for the purpose of piercing the sealable septum of a vial and directing the filtered liquid into the vial or another suitable container for further analysis.

12 Claims, 1 Drawing Sheet

LIQUID COLLECTOR PRESSURIZING AND FILTERING MEANS

TECHNICAL DISCLOSURE

A liquid sample bailer is adapted to be immersed into and removed from a body of liquid, collect and contain a sample of the liquid therein to be tested. Thereafter, a liquid pressurizing device and a filter unit are quickly attached to the bailer and adapted to filter out particles of suspended materials which may be present in the liquid sample before doing a further analysis of the filtered liquid.

BACKGROUND OF THE INVENTION

1. Field of Invention

The invention relates to testing of liquids such as ground water for contaminants and other dissolved materials.

2. Description of the Prior Art

There have been many systems devised for monitoring contamination of liquids, especially for field testing ground water for dissolved metals. However, most devices and processes heretofore devised such as disclosed in U.S. Pat. Nos. 4,430,213 and 4,590,810, are not easily adaptable to taking and filtering of liquid and thus have been slow and time consuming and too cumbersome to use in the field. It is, therefor, the object of this invention to provide apparatus adaptable to speed up the testing process while maintaining and improving the integrity of the fluid sample during filtration thereof. For example, filtration with a conventional vacuum or pressurized system can take, if everything goes right, 15 to 30 minutes and thus jeopardize field sample integrity. The instant invention has reduced the field sample preparation time for dissolved metals testing by at least 50% at no extra cost and minimized the risk of further contamination of the samples. As done in the prior art, there is no need to pour the sample from the bailer into a separate filter unit and thereby risk further contamination. Instead, the instant invention provides means to pressurize the bailer, attach a filter unit directly to the pressurized bailer and thereby cut the testing and filtration time for a typical liter sample of groundwater to just 5 to 10 minutes and this minimizes handling time. The liquid sample under low pressure flows directly from the bailer through the filter and into a container or sealable vial.

SUMMARY OF THE INVENTION

A combination pressurized liquid bailer and filtration device in which a liquid sample bailer is adapted at its lower end with a check valve therein that allows liquid into the chamber when immersed and lowered into a body of liquid and which automatically closes and traps the liquid sample therein when lifted or removed from the body of liquid.

A separate filter unit including upper and lower connecting means adapted to be push fitted into the lower end portion of the bailer comprises a disposable polymeric filter element within a housing attached at its lower end to a flow control valve from which filtered liquid flows into a container or sealable vial.

A pin in the upper connector extends to raise and open the check valve in the lower end of the bailer and thus allow liquid flowing into and through the filter element below. At its upper end portion the bailer has wall surfaces about a precision opening or bore therein adapted to receive and sealably engage a connector plug and tubing attached to either a low pressure hand operated pumping unit or a small regulated tank of inert compressed gas which pressurizes the fluid sample in the bailer and causes it to flow through the filter unit below and into a container.

DESCRIPTION OF THE PREFERRED EMBODIMENT(S)

Figure 1:
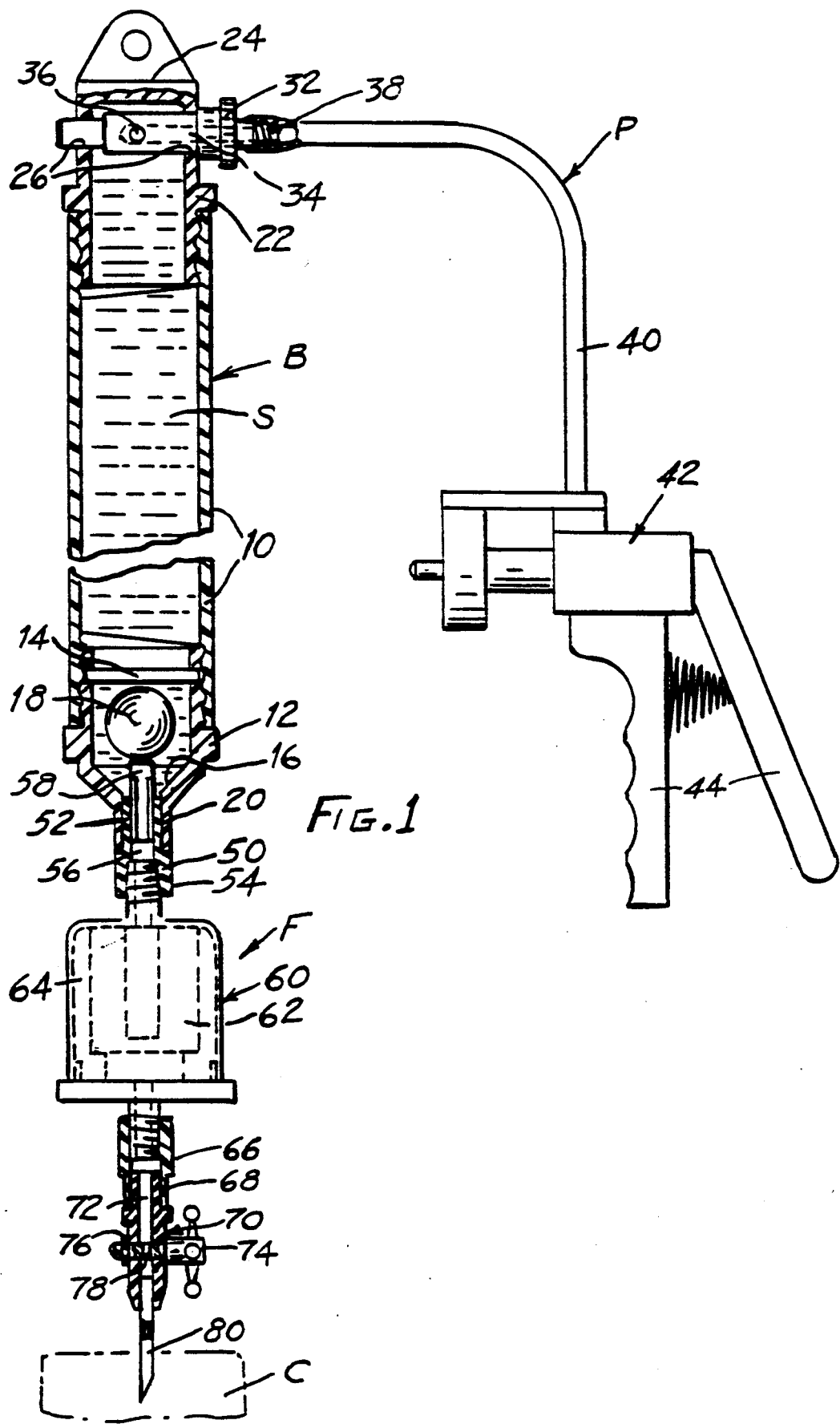
FIG. 1 is a view partly in section of the apparatus of the invention comprising an assembled combination of a bailer connected to both a pressurizing unit and filtering device.

In the drawing there is shown a typical bailer B which comprises an elongated hollow tube or body 10 about 1¾" (4.45 cm) in diameter and one foot (0.305 m) long is internally threaded and/or adapted at its lower end portion to receive a lower check valve housing 12 including a ball or poppet retaining cross pin or stop means 14, a ball or poppet seat 16 engageable by a ball or poppet 18 to close off the internal opening 20 in the lower end portion of the valve housing 12 which alternatively may be made as an integral part of the tubular body. At its upper end portion the bailer 10 is also internally threaded and/or adapted to receive a hollow top connector or housing 22 which also may be an integral part of the tubular body. The top housing 22 has a top wall 24 adapted to be attached to a line or the like and to close off the internal bore below and connector means comprising walls or surfaces about a precision cross bore 26 adapted to allow fluid such as air to enter and exhaust therefrom when the bailer B is lowered into and lifted, in the well known manner, from a body of liquid to be tested and before the liquid sample taken is to be pressurized and filtered as hereinafter disclosed.

It should be thus clear up to this point and during the taking of a liquid sample that the bailer B comprises, check valve housing 12 and the associated check valve seated therein, the upper top connector 22 and its associated precision bore 26 opened and not plugged and sealingly engaged by the connector plug 32 as shown in FIG. 1.

Thus, lowering of the bailer B into a body of liquid raises the ball or poppet 18 off its seat 16 and liquid rises inside the tubular body 10 and causes fluid or air above to vent out the bore 26. When filled, the bailer is lifted, causing ball or poppet 18 to seat and trap the liquid sample therein. Once the liquid sample S is contained and the bailer B is supported in a vertical position the liquid is then ready to be filtered and also pressurized as taught herein below. To this end the upper top connector means or housing 22 and bore 26 is connected to a pressurizing means or unit P comprising a connector plug 32 inserted into and sealably engaging the internal wall surfaces about the cross bore 26. The plug 32 has a closed end and an entrance or inlet end of a fluid passage 34 extending inwardly to an outlet 36 in an intermediate portion of the plug 32 and communicates with the area within the hollow body and above the surface of the liquid sample S. The inlet end of connector plug 32 has a nipple 38 to which one end of a length of flexible tubing or conduit 40 of preferably clear plastic tubing is forced over and maintained in sealing engagement therewith. The opposite end of this tubing 40 is sealably connected to the outlet end of a commercially available hand operated piston type pump 42. Grasping and squeezing the handles 44 of this pump 42 causes a piston or diaphragm therein to be reciprocated and forces a predetermined volume of air through the tubing 40, passage 34, and out outlet hole 36 to pressurize the liquid sample, which at this point is prevented from exiting the bailer by the ball or poppet 18 seated against the ball seat 16.

Alternatively, a commercially available small tank of inert gas including the usual adjustable pressure regulator and shut-off valve connected thereto maybe substituted for the pump 42 and connected to the inlet end of the tubing 40. Thus, the liquid sample maybe pressurized at the desired pressure and volume by adjusting the pressure regulator and opening the shut-off valve accordingly.

To filter the liquid sample within the bailer there is provided a filtering device or means F which is insertable as a unit into the internal bore or opening 20 and thereby sealably connected to the lower end portion of the check valve housing 12 of the bailer B.

The filtering means F comprises an upper connector or adapter 50 having an upper portion 52 sealably engaging the inner surface of the wall about the bore 20 and extends to a larger lower internally threaded shoulder portion 54 and also has a central bore or liquid passage 56 therein. Pressed into the upper end of the passage 56 is an externally serrated or grooved pin 58 having a plurality of vertical grooves therein adapted to extend and conduct liquid from the interior of the bailer to the passage 56 and downwardly to a disposable filter unit 60 of the filtering means F.

It can be seen that once inserted into bore 20 the pin 58 engages and raises the ball or poppet 18 off the seat 16 and allows liquid to flow downwardly through the connector or adapter 50 and into the upper inlet end of the disposable filter 60. The disposable filter unit 60 has a polymeric type filter element 62 sealed within a filter housing 64 having an upper end threaded into the upper adapter 50 and a lower outlet end threaded into a lower connector or adapter 66 having a central bore 68 at the lower end thereof. Inserted into and sealingly engaged with the central bore 68 is the reduced upper entrance or inlet portion of a flow control valve 70 having a central passage or bore 72 extending therethrough to a lower outlet end portion thereof. The flow control valve 70 has a rotary valve shaft 74 extending cross wise through a valve bore in the valve 70 and held in sealing engagement with the internal surface of the valve bore by a retaining ring 76. A passage or opening 78 in the valve may be aligned with the central bore 72 to allow liquid to pass through and out a tubular tube or needle 80 inserted into the lower outlet end of the central bore 72. The tubular needle 80 may be inserted into a container C or adapted to pierce the sealable septum of a vial containing the sample for further analysis and testing of its contents.

The components of the bailer, the filter means, and the flow control valve, are preferably made of 100% virgin nontoxic fluoropolymer materials selected from nylon, polytetrofluoroethylene (Teflon), and fluorinated ethylene propylene polymer FEPP. However, the filter element is a 0.45 micron high capacity element preferably made of an inert polymeric material adapted to filter out very fine particulates of suspended materials such as metals of mercury, lead, and cadium which would alter subsequent analysis of dissolved metals.

The apparatus hereinabove described is operated as follows:

The bailer, detached from the pressurizing means, and the filter means attached to the flow control valve as a unit, is lowered by means such as a line into a body of liquid, such as water, to be tested for contaminants.

Lowering and immersing the bailer B itself into the liquid causes liquid to flow through the internal opening and raises the check valve 18 off its valve seat and fill the tubular body therewith. During filling, air or fluid is allowed to exhaust out the connecting means and bore 26 in the upper end portion. When filled, the bailer is raised and removed from the body of liquid whereupon the liquid in the bailer causes the check valve to close against the valve seat 16 and thereby retain the liquid sample taken in the bailer, preferably supported in a vertical position by any suitable means such as a stand. The filter means F and closed flow control valve are attached as a unit by pushing the upper adapter 50 thereon into sealing engagement with the lower end portion 12 of the bailer B whereupon the pin 58 thereon raises the check valve and allows liquid to flow through grooved passages in the pin 58, to the central passage 56 therein and through the filter means 60 and to the closed off flow control valve 70. The pressurizing means P is then connected as a unit by quickly inserting and pushing the connector plug 32 thereof into sealing engagement with the wall surfaces about the bore 26 in the upper end portion 22 of the bailer.

A container or vial C is then placed below or in sealing engagement with the tubular conduit or needle 80 of the flow control means to receive and contain the filtered liquid therein.

The flow control valve 70 is then opened and the fluid pump 42 operated to pump fluid into the bailer and pressurize the liquid samples therein, preferably to about 10 pounds per square inch (psi) (0.7031 Kg/cm$^2$) and thus forces the liquid S through the filter means and the liquid filtered thereby on through the flow control valve 70 and into a container or sealable vial C below. Upon filtering all or a sufficient portion of the liquid sample, the pumping is stopped, the flow control valve is closed, and the filter means F and control valve removed as a unit from the lower end portion of the bailer B. Thereafter, the filter housing 64 maybe opened and the disposable filter element 62 removed therefrom and both inspected for the presence of undesirable toxic particulates therein. The filtered water or liquid can be effectively analyzed for dissolved metals. The filter housing 60 having a filter element 62 therein maybe replaced as a unit or a new filter element 62 may be inserted into the housing. A new filter housing and filter element is then attached and the filter means made ready for filtering more of the same or another liquid sample.

The above described system and apparatus has been proven in the field by the taking of about 100 samples of ground water with a substantial saving of about 25 to 50 hours in filtration time and money.

I claim:

1. Apparatus for quickly taking and filtering toxic particulates from a sample of liquid taken from a body of liquid so that filtered liquid can then be analyzed for content of dissolved metals, comprising:

a bailer adapted to be lowered into a body of liquid and to retain a sample of the liquid therein during removal from the body of liquid including an elongated tubular body extending between an upper end portion and a lower end portion thereof, an internal opening and surrounding wall surfaces in the lower end portion allowing liquid to flow therethrough, a valve seat about an upper end of the internal opening, a movable check valve adjacent the valve seat adapted to open during liquid flow up through the internal opening and into the tubular body and to engage the valve seat to retain the liquid sample in the tubular body, connector means in the upper end portion including a fluid passage adapted to allow fluid into and out of the tubular body and for sealingly connecting pressurizing means to the bailer;

pressurizing means adapted for quick attachment to and detachment from the bailer sealingly connected to the connector means in the upper end portion for pressurizing the liquid in the tubular body;

filter means quickly attached to and detached from the lower end portion of the bailer for filtering the liquid sample including a filter housing having a lower outlet end and an upper inlet end, an adapter connected to the inlet end of the filter housing and having an inlet end portion adapted to sealingly engage wall surfaces about the internal opening and be easily connected to and disconnected from the lower end portion of bailer, a central passage therethrough and a grooved pin extending from the central passage and through the internal opening and lifting the check valve off the valve seat and having a liquid passage connected to the central passage; and a flow control valve with a liquid passage therethrough sealingly connected to the lower outlet end of the filter housing and adapted selectively to prevent and to allow filtered liquid to flow therethrough and into a container.

2. Apparatus according to claim 1 wherein the bailer further comprises:

stop means in the lower end portion for limiting movement and opening of the check valve during flow of liquid into the tubular body.

3. Apparatus according to claim 2 wherein the check valve is a ball or poppet valve.

4. Apparatus according to claim 3 wherein the valve seat is a surface extending continuously about the upper end of the internal opening.

5. Apparatus according to claim 1 wherein the connector means comprises:

sealingly engageable surfaces of a wall about a bore in the upper end portion of the bailer.

6. Apparatus according to claim 5 wherein the pressurizing means comprises:

a connector plug having an outer open end and an inner closed end, a fluid passage extending from the outer open end to and out an intermediate portion of the connector plug, and the connector plug is adapted to be inserted into and sealingly engage the surface of the wall about the bore in the upper end portion;

a tubular conduit having an inlet end and an outlet end sealingly connected to the outer open end of the connector plug and a fluid pump having a fluid intake opening and a fluid outlet end portion connected to the inlet end of the tubular conduit and adapted to pump fluid into the tubular body and pressurize the liquid sample therein.

7. Apparatus according to claim 5 wherein the pressurizing means comprises:

a connector plug having an outer open end and an inner closed end, a fluid passage extending from the outer open end to and out an intermediate protion of the connector plug, and the connector plug is adapted to be inserted into and sealingly engage the surface of the sall about the bore in the upper end portion;

a tubular conduit having an inlet end and an outlet end sealingly connected to the outer open end of the connector plug and a tank of inert compressed gas including an adjustable pressure regulator and shut-off valve and a fluid outlet end portion thereon, connected to the inlet end of the tubular conduit and adapted upon opening the shut-off valve to allow the gas to flow into the tubular body and pressurize the liquid sample therein.

8. Apparatus according to claim 1 wherein the filtering means further comprises:

a disposable filter element contained in and removable from the filter housing to remove the presence of any undesirable toxic particulates filtered from the liquid sample.

9. Apparatus according to claim 8 wherein the filter means further comprises:

a lower adapter connected to the lower outlet end of the filter housing and having a central passage therethrough and a lower outlet end portion sealingly connected to an upper inlet end portion of the flow control valve.

10. Apparatus according to claim 9 wherein the bailer including the tubular body, the upper end portion, the lower end portion, the check valve and seat and stop means and the filter means including the upper and lower adapters, the filter housing, and the flow control valve, are all made of inert a non toxic fluoropolymeric material.

11. Apparatus according to claim 10 comprising a tubular conduit of nontoxic material extending from the lower outlet end of the flow control valve and having an outlet end adapted to pierce and sealingly engage a self sealable septum of a vial for receiving and containing the liquid sample.

12. Apparatus according to claim 8 wherein the filter element is made of a polymeric material adapted to filter particulates as small as 0.45 micron from the liquid sample.

* * * * *